United States Patent [19]
Borza

[11] Patent Number: 5,995,874
[45] Date of Patent: *Nov. 30, 1999

[54] TRANSCUTANEOUS ENERGY TRANSFER DEVICE

[75] Inventor: Michael Andrew Borza, Ottawa, Canada

[73] Assignee: DEW Engineering and Development Limited, Ottawa, Canada

[*] Notice: This patent is subject to a terminal disclaimer.

[21] Appl. No.: 09/020,805

[22] Filed: Feb. 9, 1998

[51] Int. Cl.$^6$ ........................................... A61N 1/02
[52] U.S. Cl. ................................................... 607/61
[58] Field of Search ........................ 607/32, 31, 61, 607/60; 128/899

[56] References Cited

U.S. PATENT DOCUMENTS

| | | |
|---|---|---|
| 4,082,097 | 4/1978 | Mann et al. . |
| 4,665,896 | 5/1987 | LaForge et al. . |
| 4,697,183 | 9/1987 | Jenning et al. ............... 340/870.25 |
| 4,924,171 | 5/1990 | Baba et al. .................. 323/347 |
| 5,350,413 | 9/1994 | Miller ............................ 607/61 |
| 5,450,076 | 9/1995 | Donig et al. ................ 340/870.39 |
| 5,495,241 | 2/1996 | Donig et al. ................ 340/870.39 |
| 5,630,836 | 5/1997 | Prem et al. .................... 607/61 |
| 5,713,939 | 2/1998 | Nedungadi et al. ............ 607/33 |
| 5,713,954 | 2/1998 | Rosenberg et al. ............. 623/3 |
| 5,741,316 | 4/1998 | Chen et al. .................... 607/61 |
| 5,755,748 | 5/1998 | Borza ............................ 607/61 |

FOREIGN PATENT DOCUMENTS 32 20 930 A1  12/1983  Germany .

OTHER PUBLICATIONS

N. de N. Donaldson, "Use of feedback with voltage regulators for implants powered by coupled coils," *Medical & Biological Engineering & Computing*, Vol. 23, May 1985, p. 291.

*Primary Examiner*—Scott M. Getzow
*Attorney, Agent, or Firm*—Neil Teitelbaum & Associates

[57] ABSTRACT

In the design of transcutaneous energy transfer devices variation in spacing between the coils results in energy transfer efficiency changes. These changes may have other causes. It is proposed to use an autotuning circuit and a voltage control circuit in cooperation with feedback from the internal coil in order to better maintain energy transfer levels as desirable. The feedback is typically provided via IR communication; however, when skin is highly pigmented, IR communication is inefficient. A method and system for using RF signals to accomplish the communication is disclosed.

11 Claims, 10 Drawing Sheets

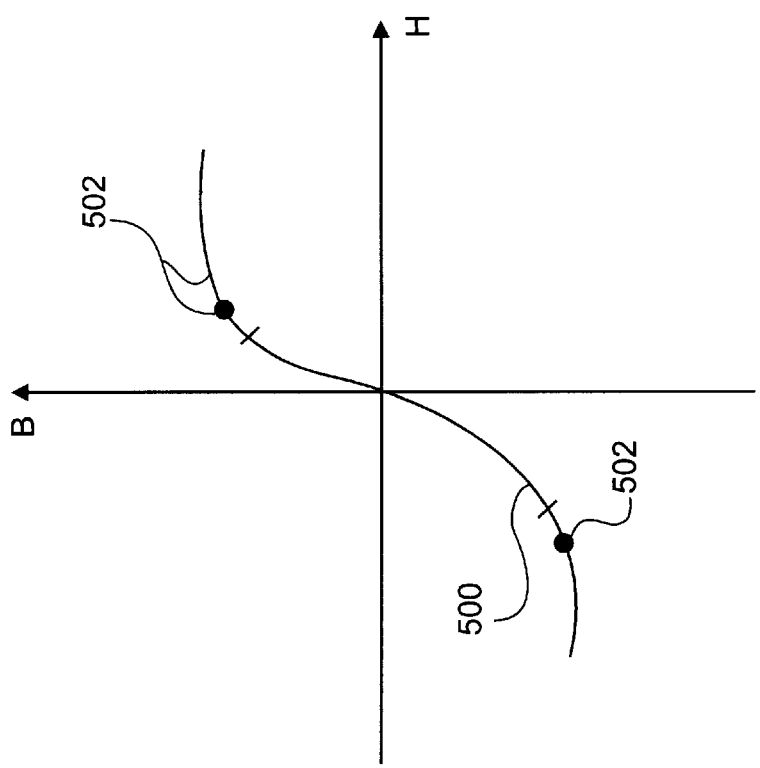

TRANSCUTANEOUS ENERGY TRANSFER DEVICE

FIELD OF THE INVENTION

This invention relates to the field of medical devices. In particular, the present invention relates to transcutaneous energy transfer (TET) devices.

BACKGROUND OF THE INVENTION

A TET device is a device for providing electrical power to an implanted mechanical or electrical medical device, such as a bone growth stimulator, muscle stimulator, prosthetic heart or a ventricular assist device, without having to breach the skin to lead conducting wires therethrough.

In U.S. Pat. No. 5,350,413 John Miller discloses a TET device with a high-energy transfer efficiency. Such a device allows for efficient transfer of energy between two coils having fixed spacing. Unfortunately, as one coil is located within a body and another coil is located outside the body, maintaining coil separation at a constant distance is difficult. Changes in coil spacing result in variation of the induced voltage and, as the distance increases, the power transfer efficiency drops off rapidly.

In an article entitled "Development of an Autotuned Transcutaneous Energy Transfer System," John Miller, G. Belanger, and T. Mussivand suggest an autotuning circuit to overcome this problem. The autotuning circuit compares various voltages and currents present within a driving circuit external to the body to determine a tuning requirement. Such tuning enables the tuning of energy transfer where the coil spacing varies.

It has been found that the autotuning function disclosed addresses the problem of power coupling efficiency, but fails to address a fuirther problem of internal voltage control. In driving implanted medical devices, energy coupling efficiency and voltage control are separate but related issues to address. Coupling efficiency results in lower operating cost and improved battery life. Voltage control results in improved device operation and increased safety. In fact, some devices will fail from excessive applied voltage.

Further, it has been found that efficiency is affected by several factors, some of which include power coupling related factors such as spacing, and load related factors such as medical device load requirements or faults. Unfortunately, autotuning does not address the issue of providing additional energy when required by a medical device.

In U.S. Pat. No. 5,350,413, John Miller further discloses an IR telemetry module for providing bidirectional communications. It is known that infra red telemetry is affected by skin pigmentation. As a transceiver disclosed by John Miller is implanted beneath a layer of skin, such considerations are important. It has been found that highly pigmented skin attenuates IR signals and renders a system as disclosed by John Miller substantially unworkable. Further, dirt and other obstructions like clothing or casings affect IR telemetry and can render it inoperable. For a television remote control, this is an acceptable limitation; for medical devices required by an individual, an inoperable TET is unacceptable.

Limitations are inherent in an IR telemetry link. IR is an optical communications means requiring an optical path between transmitter and receiver. Absent fibre or waveguides, IR telemetry is highly directional and limits a system to a single transmitter operating at a time in a direction. The directional nature of IR telemetry requires substantial alignment for optical communication Until recently, IR telemetry has been limited to low frequency communications. At low frequencies, it is difficult to multiplex channels as a serial link requires higher frequencies than a true multi-channel implementation. Unfortunately, as noted above, IR telemetry is not suited to true multi-channel communications. The advent of high speed IR circuits may allow for channel multiplexing using a known technique such as time division multiplexing (TDM); however, this does not overcome previously mentioned shortcomings of IR.

OBJECT OF THE INVENTION

Thus in an attempt to overcome these and other limitations of the prior art it is an object of the present invention to provide a TET with voltage control and autotuning in order to improve adaptability and in order to improve energy transfer capability.

Thus in an attempt to overcome these and other limitations of the prior art it is a further object of the present invention to provide a bidirectional communication link capable of transmitting through skin regardless of pigmentation. It is a further object of the present invention to provide an omni-directional bi-directional communication link.

SUMMARY OF THE INVENTION

An advantage of the present invention is that it is capable of reacting to a variety of feedback from an internal coil or telemetry circuitry associated therewith thereby improving its ability to meet energy transfer requirements.

A further advantage of the present invention is that it is capable of providing a bi-directional communication link between each part of a TET that is less sensitive to skin pigmentation than IR.

In a first broad aspect, the invention seeks to provide for a TET device having a primary coil and a primary coil driver for operation outside a living organism, and a secondary coil for implanting within the living organism the two coils for being coupled by a magnetic field, a system for tuning the TET device comprising:

a) means for measuring at least a characteristic of the secondary coil during operation and for transmitting an indication of the characteristic from within the organism to outside the organism;

b) means for receiving the transmitted indication of the characteristic and for providing a signal related to said indication; and, c) a control circuit for receiving the signal related to said indication and for controlling a characteristic of the magnetic field in order to effect a change in the saturation point of the magnetic field.

In another broad aspect, the invention seeks to provide for a TET device having a primary coil and a primary coil driver for operation outside a living organism, and a secondary coil for implanting within the living organism the two coils for being coupled by a magnetic field, a system for tuning the TET device comprising:

a) means for measuring at least a characteristic of the secondary coil relating to power coupling efficiency during operation and for transmitting an indication of the characteristic from within the organism to outside the organism;

b) means for receiving the transmitted indication of the characteristic and for providing a signal related to said indication; and, c) a control circuit for receiving the signal related to said indication and for effecting a change in the saturation point of the magnetic field.

In yet another broad aspect, the invention seeks to provide for a TET device having a primary coil and a primary coil driver for operation outside a living organism, and a secondary coil for implanting within the living organism, a system for tuning the TET device comprising:

a) means for measuring at least a characteristic of the secondary coil during operation and for transmitting an indication of the characteristic from within the organism to outside the organism;

b) means for receiving the transmitted indication of the characteristic and for providing a signal related to said indication; and, c) a voltage control circuit for receiving the signal related to said indication and for controlling voltage and current in the primary coil in dependence upon the received signal.

BRIEF DESCRIPTION OF THE DRAWINGS

Exemplary embodiments of the invention will now be described in conjunction with the following drawings, in which:

FIG. 6b is a graph of a real B-H curve;

Detailed Description of the Invention

Figure 1:
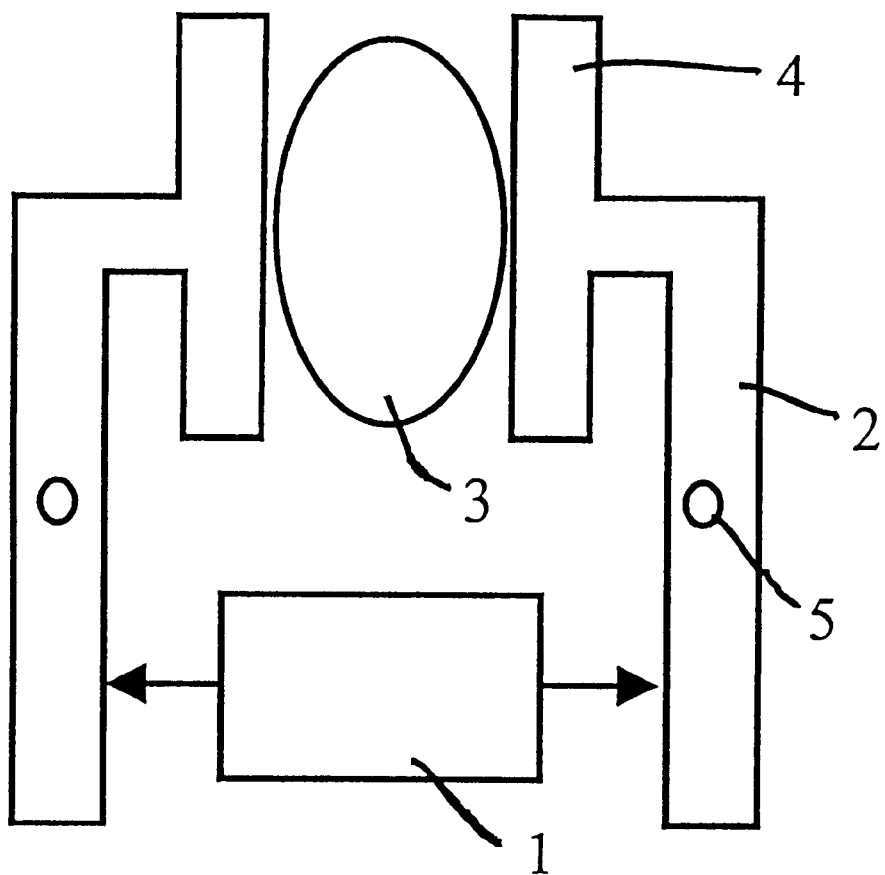
FIG. 1 is a simplified diagram of a Baxter Pharmaceutical® pump.

Referring to FIG. 1, a Baxter Pharmaceutical® Pump is shown. The heart assist device operates to pump blood within a body. A solenoid 1 separates two levers 2. At an opposite end, the levers 2 are connected to compression means in the form or plates 4 that push against a sack 3. The compression of the sack 3 results in a pumping action. A fulcrum 5 is shown in order to clarify the motion of the levers 2.

This pumping action requires that the solenoid 1 receive adequate power. The solenoid 1 is provided power in an alternating fashion. Power is only provided while the solenoid 1 exerts force on the levers 2. Alternatively, power is provided all the time and the device converts the power signal into alternating power. The conversion can be accomplished using energy storage and discharge means. Once the sack 3 is compressed, the solenoid must be turned off to allow the sack 3 to fill with fluid. Further, the solenoid 1 draws little power except when compressing the sack 3. Even during compression, power requirements vary throughout a stroke. The operation is well documented in the prior art.

The operation of the pump and similar devices draws energy inconsistently. As the load increases, voltage in the power supply is affected as is drive current. Increasing power supply voltage may result in voltage spikes when the load is removed. These power spikes are capable of damaging some devices. An approach to preventing this problem is to include voltage regulation means within each device to protect against power surges and voltage spikes. According to the present invention, a method is disclosed wherein voltage is regulated through a feed back loop that monitors load and induced voltage and thereby, as load drops off induced voltage is maintained.

Figure 2:
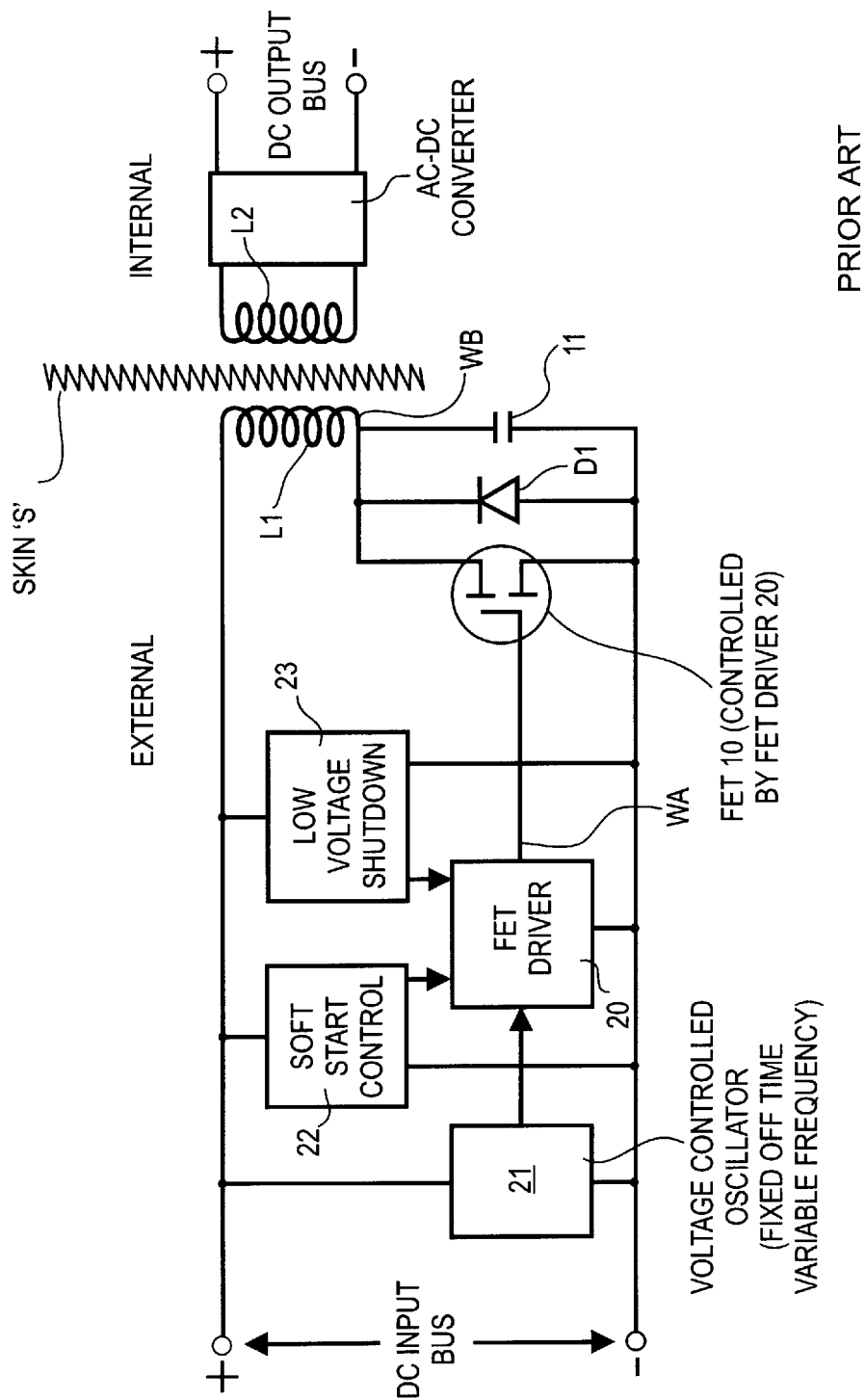
FIG. 2 is a circuit diagram of a TET according to the prior art.

Referring to FIG. 2, a TET device known in the prior art is shown. The device comprises a transformer designed to induce AC current in a subcutaneous winding, for transformation to DC voltage for use in powering a medical device. Alternatively, the induced AC current is used to power a medical device. AC current is induced in L2, the secondary winding which may be for instance a torus core, wound with Litzendraht wire implanted just beneath the surface of the skin S with electrical leads connected to a medical device. A similar primary winding L1 is located in alignment with the secondary winding, on the skin surface and exterior thereto.

Primary winding L1 is connected to a capacitor 11 that is connected to the negative of a DC input bus. As indicated in FIG. 2, winding L1 is also connected to a field effect transistor (FET) 10 controlled by FET driver 20. FET driver 20 receives inputs from voltage controlled oscillator 21, soft start control 22 and low voltage shutdown 23 to produce an alternating or pulsing waveform.

Power transfer may be considered to take place in two phases, a storage phase and a resonant phase. During the storage phase, energy is stored in the primary coil using a FET to switch the coil directly across the DC input supply. The FET is selected for its very low "on" resistance to minimise conduction losses.

As shown in FIG. 2, the coil L2 is implanted under the skin S. The remainder of the circuit remains external to the skin. Voltage is induced in the coil L2 from the coil L1, said coil and driver circuitry therefor remaining external to the skin S. Skin is capable of suffering damage from exposure to electrical fields for prolonged periods of time. Therefore, in designing TET devices, it is very useful to limit the electrical field necessary to induce sufficient voltage to provide necessary power.

Figure 3:
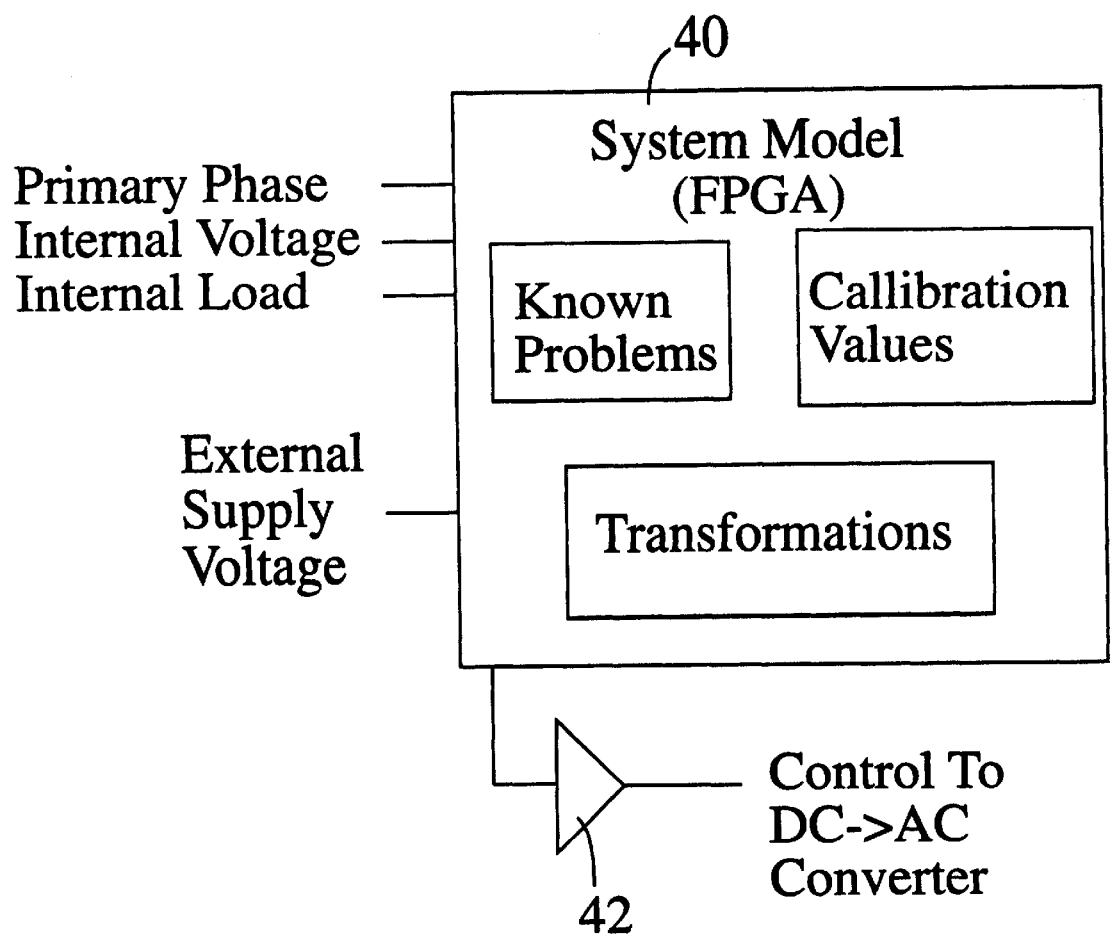
FIG. 3 is a block diagram of an integrated voltage control and autotuning circuit implemented in an FPGA.

Referring to FIG. 3, an integrated voltage control autotuning circuit implemented in an FPGA is shown. Measurements of internal voltage and internal load are supplied to the control circuit via a telemetry link with a subcutaneous circuit (shown in FIG. 4). Such telemetry links are known using IR transmission. Based on the supplied values, the control circuit assesses the voltage control needs and the coupling efficiency in order to maintain appropriate levels of energy for the medical device. The FPGA controls the DC to AC converter, in the form of an FET driver 20 and a power control circuit 43 (shown in FIG. 4), based on these values and based on system knowledge or calibration values. The FET driver 20 is also used to control frequency and off time. The circuit within the FPGA may incorporate other aspects of the TET circuitry.

A form of autotuning is known in the prior art. Since a TET system must operate over various conditions, it is preferable that a controller has knowledge of current conditions in order to set the correct operating point. In order to effectively control voltage and autotune the TET, feedback is required from the coil L2. This feedback and a circuit designed to correct voltage and to tune the circuit based on the feedback together allow for improved operation of the TET.

In operation, the programmable circuit responds to the measured values. When two values are measured in the form of load current and voltage, the measured values are low, normal, or high resulting in 9 possible combinations. In this example, phase is corrected using phase correction circuitry independent of the programmable circuit. For each of the 9 possible combinations the programmable circuit responds. The response may, for example, drift values toward an acceptable range. When measured load increases, in the example, induced current is increased to maintain induced voltage substantially constant. When measured voltage increases, induced voltage is lowered to maintain induced voltage substantially constant. This effectively improves operation of the TET and prevents surges that can damage implanted devices.

Alternatively, the programmable circuit responds to a plurality of measured values. Alternatively, the programmable circuit also contains a feedback loop to respond to current and past measured values. Alternatively, the programmable logic is calibrated to function with a specific implanted device; the calibration is undertaken during an initial period of use. A calibrated programmable circuit allows for corrective actions in anticipation of change. The system, for example, includes storage means for storing past sequences of measured values that were controlled inadequately. When these patterns occur, the programmable circuit responds differently than in previous attempts (within acceptable parameters) to better address the measured values.

Low internal voltage is caused by poor coupling or by high internal load. Providing both voltage and load from the internal coil to the external control circuit thereby allows for assessment of cause and appropriate control response.

Figure 4:
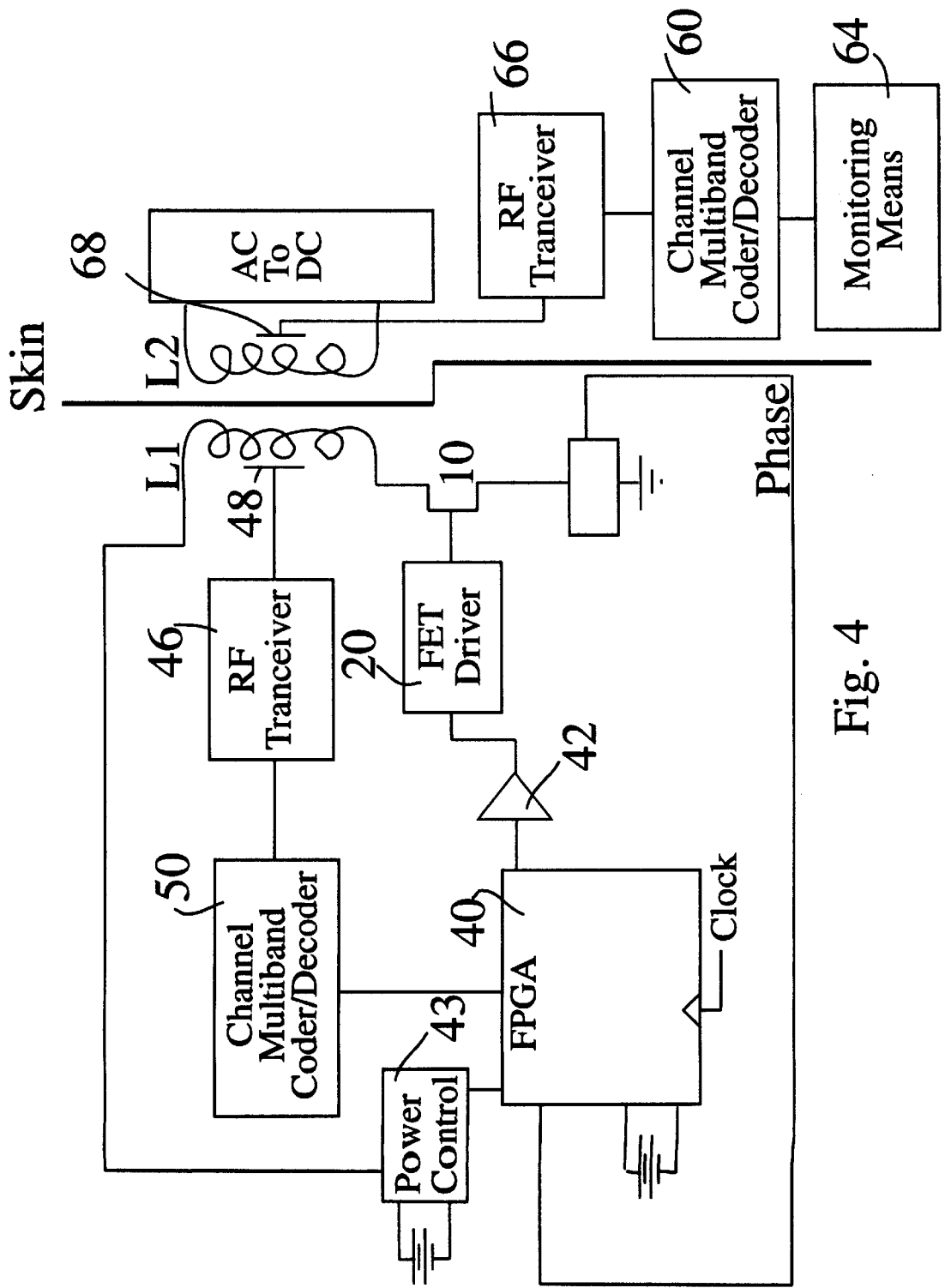
FIG. 4 is a partial circuit diagram of an RF telemetry system according to the present invention.

Turning to FIG. 4, a block diagram of a TET system according to an embodiment of the present invention and incorporating the programmable circuit of FIG. 3 is shown. The programmable circuit 40 in the form of an FPGA drives an FET driver 20 and a power control circuit 43. The FET driver 20 switches a transistor 10 to drive the primary coil L1 in an alternating fashion. The power control circuit 43 controls current and voltage provided to the coil L1 when FET 10 is switched "on." The programmable circuit 40 receives inputs comprising timing in the form of a clock, power in the form of a voltage input, and monitored values received from a subcutaneous circuit via a telemetry link. The control functions within the programmable circuit 40 are dependent upon the received signals.

Certain limitations are inherent in an IR telemetry link. IR is an optical communications means requiring an optical path between transmitter and receiver. Absent fibre or waveguides, IR telemetry is highly directional and limits a system to a single transmitter operating at a time in a direction. The advent of high speed IR circuits allows for channel multiplexing using a technique known as time division multiplexing (TDM). This allows for multi-channel operation in some limited cases but does not overcome other previously mentioned shortcomings. Though a telemetry link in the form of an RF telemetry link is shown in FIG. 4, with the programmable circuit 40 any telemetry link providing a capability to transmit or receive all necessary monitored information will work. It is, however, preferable to use a true multi-channel communications means according to the present invention.

The RF transceiver 46 receives a signal via an antenna means 48 in the form of an RF antenna tuned to a predetermined frequency. Alternatively, the antenna means forms an integral part of the primary coil L1 (shown in FIG. 5). The received RF signal (at the RF transceiver 46) is filtered to reduce noise and remove unnecessary signals. Alternatively, this step is performed in the channel multi-band encoder/decoder 50. It is then decoded into individual channels or individual monitored values.

The channel structure of the information incorporates a channel for control information and a plurality of channels for monitored information. Control information is transmitted from the external circuit to the subcutaneous circuit. The subcutaneous circuit transmits diagnostic indicators in the form of bearing condition, blood sack shape, and device failure to the external circuit. Alternatively, the internal circuit sends control signals as well as diagnostic signals to the external circuit. In order to send a plurality of monitored values via a single channel, a method such as time division multiplexing (TDM) is employed. Using TDM, each value is assigned a time slot that repeats every frame. Within each frame a plurality of time slots each contains a value indicative of a measured or monitored characteristic. In each frame, the order of the plurality of channels is the same and, therefore, a value for each monitored characteristic is obtained by sampling the channel for that characteristic.

An example will demonstrate TDM. When 8 channels are within each frame, any value can be sampled based on the frame's frequency. Commonly, a frame pulse or a frame indicator signal is incorporated in order to align a transmitter and a receiver. From a frame's beginning a first channel value is sampled. From a frame's beginning+$\Delta t(n/8$ of a frame's period) an nth channel is sampled. In this way, a plurality of channels is transmitted across a single physical channel using serial communications. It is preferable to maintain at least some channels for security information to ensure that the telemetry link is between predetermined circuits. This is to minimise effects of stray signals.

A subcutaneous circuit comprises a secondary coil L2 similar to the primary coil L1. An antenna 68 is disposed near the secondary coil L2 and in co-operation with an RF transceiver 66 sends monitored signals to the external circuit. Alternatively, monitored signals and control signals are transmitted. Alternatively, the secondary coil L2 also acts as the antenna. As with the external received and transmitted signals, noise is present in the subcutaneous received and transmitted signals in the form of white noise and cross talk from the power signal. A channel multi-band encoder/decoder 60 filters the noise and extracts desired signals. The channel multi-band encoder/decoder 60 also encodes monitored values to form appropriate RF signals in order to improve transmission effectiveness. Means such as forward error correction or parity are employed to improve the accuracy of the received and decoded signals.

The cross talk induced in a received signal is significant. A TET transmits energy via a primary and a secondary coil. The energy transferred is often over 50 watts. The RF telemetry signal required to communicate between subcutaneous and external circuits transmits at a power level of several milliwatts. It is therefore important to shield circuitry (both external and subcutaneous) to ensure that once filtered, cross talk is not reintroduced. In a further embodiment, monitoring characteristics of at least some of the RF signals received, transmitting values in dependence upon the characteristics, and varying the RF signal parameters in the form of strength and frequency are implemented to improve telemetry robustness.

The channel multi-band encoder/decoder 60 receives information to encode for transmission from the monitoring means 64. The monitoring means for voltage and current form part of the AC to DC converter circuit when one exists. Alternatively, separate monitoring means are implemented. Of course, monitoring means are implemented to monitor any characteristic desirable in the subcutaneous circuit and in the implanted medical device.

Figure 5:
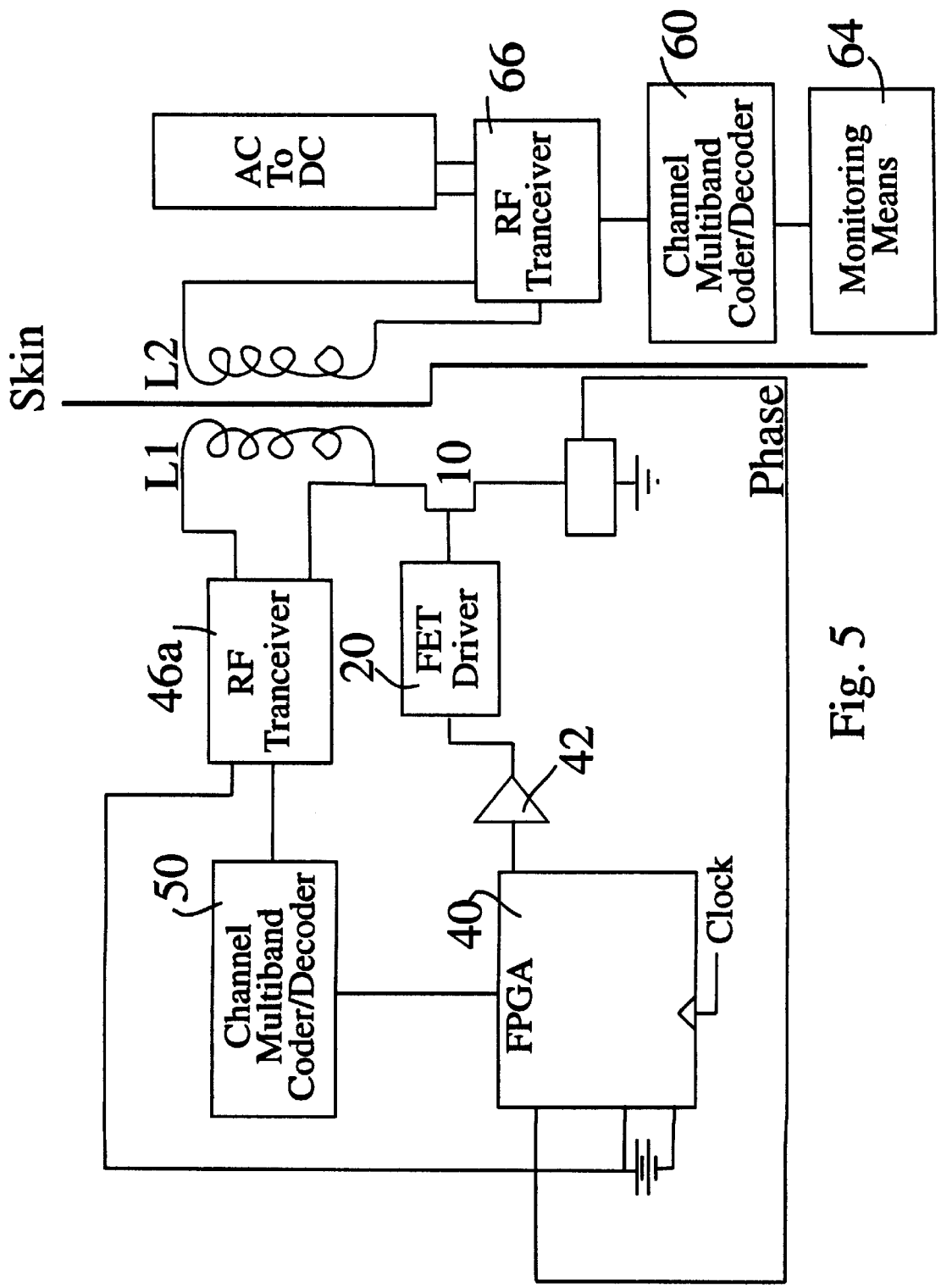
FIG. 5 is a partial circuit diagram of an alternative RF telemetry system according to the present invention.

Referring to FIG. 5, an RF telemetry system is shown comprising an internal coil L2 and an external coil L1. Monitoring and control signals transmitted from the external coil L1 to the internal coil L2 are superimposed upon a power coupling signal to provide communication using the coils L1 and L2 as antennas. When the monitoring and control signals have a high frequency relative to the frequency of the power signal, a low pass filter is used to remove the power signal. Otherwise known frequency modulation (FM) techniques are used to separate the signals. In the diagram of FIG. 5, an RF transceiver circuit 46a acts to drive the coil L1 providing power thereto as well as communications signals. Such a circuit superimposes the power to be coupled between the coils and communications signals. This is necessary in the absence of a separate transmitting antenna.

The use of RF telemetry is possible because of known characteristics of TETs. The power signal is generally well understood during design. An RF monitoring and control channel is preferably very low energy (milliwatts) whereas the power signal requires significant energy to drive an internal device. The RF telemetry signals are shortrange signals transmitted at high frequencies such as those in the GHz range. Alternatively, other predetermined frequencies are used. As such, the cross talk induced by the power signal must be filtered or distinguished in order to be extracted. It is well known within the art of RF communications to provide low pass filters or to extract a known frequency from a signal.

Using RF telemetry provides many advantages. Multiple channels can be used for multiple signals allowing a large number of characteristics to be monitored and communicated. Further, an RF system allows control and monitoring signals to be separated onto different channels. Further, RF transmissions are not substantially attenuated by skin and are relatively pigmentation independent. This allows RF signals to be transmitted across a barrier, to a receiver misaligned from a source, and in the presence of dirt.

Preferably, as shown in FIG. 4, separate antennas are used improving frequency response and signal to noise ratios. The separate antennas are tuned for at least a transmission frequency. Tuning reduces the power requirements for driving the antennas and improves the quality of received signals. Small RF antennas are located near the coils L1 and L2. This requires little space, is inexpensive to manufacture, and improves operation of the communication system. Alternatively, a plurality of antenna pairs is used to transmit and receive signals.

In association with the improved power coupling control mechanism described herein, the RF telemetry system allows for a sufficient number of characteristics such as phase, voltage, drive current, bearing wear, battery status, and other non-essential characteristics such as blood flow, or muscle contraction. Each said characteristic is monitored internal to a body and transmitted via RF telemetry to an external control and monitoring circuit. Alternatively, external monitoring is also performed to indicate power signal voltage, communications signal strength, etc. and transmit monitored values via RF telemetry to a subcutaneous circuit. The use of RF telemetry, allows for each monitored characteristic to occupy a single channel or alternatively, for multiplexing a plurality of characteristics onto a single channel using a known method such as TDM.

Using RF telemetry, it is preferable to maintain a security ID or another form of transmitter verification to prevent effects of stray signals and to limit circuit response to signals originating from an appropriate transmitter.

Figure 6A:
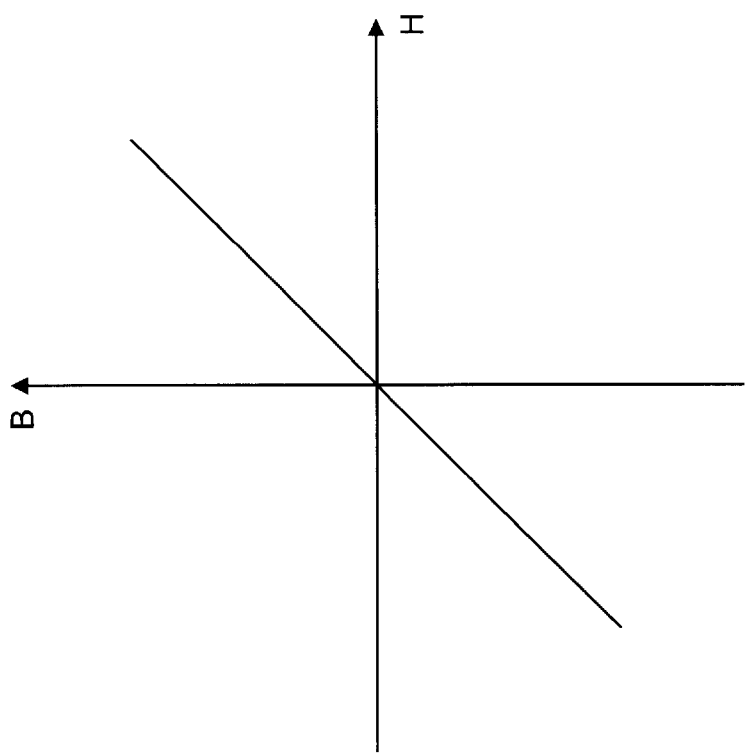
FIG. 6a is a graph of an ideal B-H curve.

Saturation of magnetics is a serious concern in transmitting power using magnetic fields. Referring to FIG. 6a, an ideal normal magnetising curve (Flux density (B)-magnetic field intensity (H) curve) is shown. As is evident to those of skill in the art, the linear nature of the graph is only accurate when the permeability $\mu$, which is equal to B/H, is constant over the entire range of the graph. Ideal normal magnetisation curves are useful to understand basic magnetic fields and to approximate performance within a generally linear range of a real normal magnetising curve. Referring to FIG. 6b, a normal magnetising curve illustrating the effects of saturating magnetics is shown. Over a linear range 500, power provided to the magnetic field appears within the field. At a point 502, $\mu$ begins to change significantly and non-linear effects of magnetic field saturation become significant. Here power provided is not efficiently transferred into the magnetic field.

Different media result in different normal magnetising curves. Magnetic media such as sheet steel or iron have nonzero retentivity, which allows formation of permanent magnets. Non magnetic media, have less steep normal magnetising curves since the media itself does not retain magnetic characteristics.

Many factors contribute to the shape of the normal magnetising curve. For example, magnetic field geometry, medium material, core material, and frequency and shape of the power wave provided to the field effects the B-H curve. An overview of B-H curves and magnetic coupling is provided in Chapter 17 of Carlson, Bruce; Gisser, David; *Electrical Engineering Concepts and Applications*, 1981 which is incorporated herein by reference. These effect the location of the point 502 where efficient energy transfer is no longer possible because $\mu$ is varying substantially over its value in the linear region.

In a TET device, the secondary (implanted) coil is driven by a magnetic field generated by the primary coil. Some magnetic field geometries are more efficient than others. Generally, an efficient field geometry is generated for coupling the coils; however, by evaluating overall efficiency of the TET system and not simply magnetic field generation efficiency, advantages are achieved.

Since the human body comprises significant quantities of iron, various salts, and water, the properties of human tissue have an effect on a magnetic field passing therethrough. The iron, a magnetic material, has a steep B-H curve because of its retentivity, $B_r$. Water also has some polarisation and therefore effects the magnetic field. These properties result in magnetic field saturation beyond certain field strengths. It would be desirable to provide a TET device capable of more efficiently transferring energy to an implanted coil.

Figure 7:
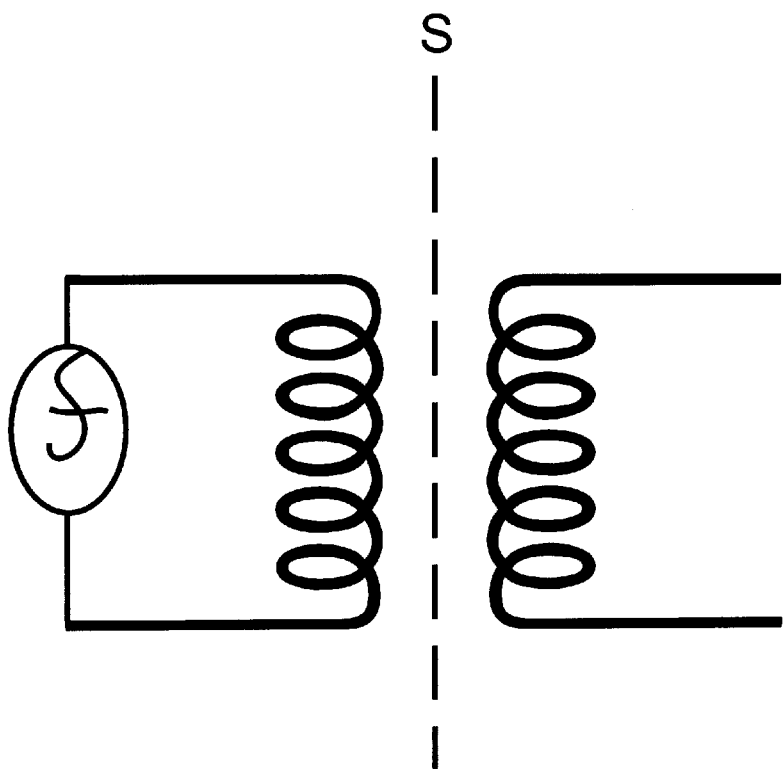
FIG. 7 is a simplified diagram of a TET system according to the present invention comprising a coil pair wherein the primary coil is driven by a variable frequency signal.

Referring to FIG. 7, a pair of TET coils is shown. The primary coil is driven by a wave having variable frequency.

By varying the frequency the B-H curve is varied. This allows for an increase or decrease to the substantially linear portion 500 of the B-H curve. Of course, varying the B-H curve effects field generation efficiency.

As disclosed above, there are several significant factors in assessing TET system efficiency including efficiency of power transfer from the power source to the secondary coil, efficiency of power transfer across the skin, and tissue longevity/damage. In order to improve overall coupling from the power source to the secondary coil, both magnetic field generation efficiency and coupling efficiency are of concern. When a TET device is operating within the saturation of magnetics region of the B-H curve, coupling efficiency is greatly reduced. Therefore, it is advantageous to reduce the efficiency of providing power to the magnetic field in order to move the saturation region of the B-H curve and thereby increase coupling efficiency. Of course, when operating within a linear portion of the B-H curve, it is preferable to increase the efficiency of providing power to the magnetic field. In this way, overall TET system efficiency is improved.

Further, skin changes over time. Within a magnetic field, skin may dry up and flake off or fall off in larger pieces. These events affect coupling efficiency and the B-H curve. By varying the frequency of the power wave provided to the magnetic field, alterations to the B-H curve are corrected, at least in part. This allows for normal operation of the TET system, even in the absence of a same medium between the coils. In order to vary the frequency, use of voltage variable capacitors in the form of varactor diodes and other known techniques allow for modulation of the capacitance in order to provide a high degree of tuning of the resonant frequency of the drive circuit. Of course, other frequency variation techniques may also be used.

Figure 8:
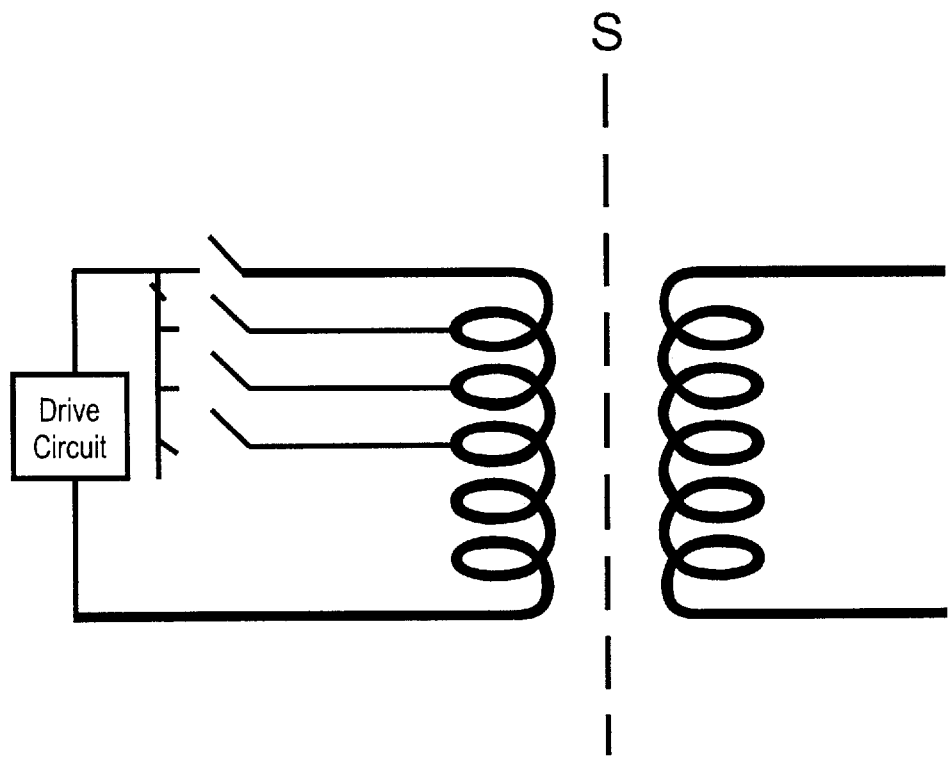
FIG. 8 is a simplified diagram of a TET system according to the present invention wherein the primary coil has a plurality of taps therefrom; and, FIG. 9 is a simplified diagram of a primary coil having a modifiable geometry for a TET system according to the present invention.

Referring to FIG. 8, a pair of TET coils is shown. The primary coil has a plurality of taps in the form of taps for each of a plurality of layers. At each layer, the tap in the form of a connection is provided to a switch. The coil is driven at one of the layers and therefore produces a magnetic field. The field shape is different depending on which layer of the coil is driven. As such, the B-H curve is also different. Modification of the B-H curve, as noted above, results in a shift of the saturation point of the curve. This allows for an increase or decrease in the maximum amount of energy that is efficiently transferred from the primary coil to the secondary coil. Experimental measurement, design analysis, and/or approximation indicate an efficiency of energy transfer from a power source in the form of a battery to the magnetic field.

When the primary coil of FIG. 8 is used, there are three switchably selectable coil geometries. Each has a measured B-H curve and a measured efficiency for driving the magnetic field. Since TET system efficiency is determined by a product of efficiencies, the efficiency of transferring power from the battery to the secondary coil is a product of the efficiency of transferring energy from the battery to the magnetic field, which is a function of coil geometry and so forth, and the efficiency of the coupling between the primary and secondary coils. Therefore, generating, with less than optimal efficiency, a magnetic field results in an increase in overall increase in efficiency when shifting of the saturation point on the B-H curve to increasing coupling efficiency results. As with many systems, since overall system efficiency is a concern, such a system is advantageous.

Often, more energy is needed than a prior art TET system can instantaneously supply. Because of field saturation, this is commonplace. Most TET devices are designed to operate within a linear range of the B-H curve. By providing a system for extending that range, a significant advantage is achieved.

Also, since skin is sensitive to electromagnetic radiation, it is possible to increase coupling efficiency at a cost of overall system efficiency and thereby reduce skin damage caused by excess magnetic field energy. Essentially, when losses due to electromagnetic field generation are significant but the saturation point is well beyond the generated magnetic field intensity, overall efficiency of the system (efficiency of the field generation x efficiency of the coupling) is reduced. Because the electromagnetic energy transmitted is thereby reduced, tissue damage is also reduced. Since tissue is one of the media within the electro magnetic field which affects saturation, it is evident that reducing the effects of saturation also reduce effects on tissue by the magnetic field. Also, when saturation is avoided, heating of the secondary coil is reduced which also reduces tissue damage.

A magnetic device always suffers losses. For example, ohmic heating results in some inefficiency. In the secondary coil, the implanted coil, this heating is detrimental to tissue life and is preferably minimised. Hysteresis loss is another source of inefficiency. Hysteresis loss is caused when a magnetic field intensity varies over time magnetising and demagnetising something within the field such as the transformer core. Eddy-current loss is caused by localised currents induced by time-varying flux. These are sources of inefficiency in field generation. For example, when using the primary coil configuration of FIG. 8, a larger coil section has a larger resistance and therefore a larger ohmic loss. Similarly, higher frequency operation results in greater hysteresis loss and so forth.

Figure 9:
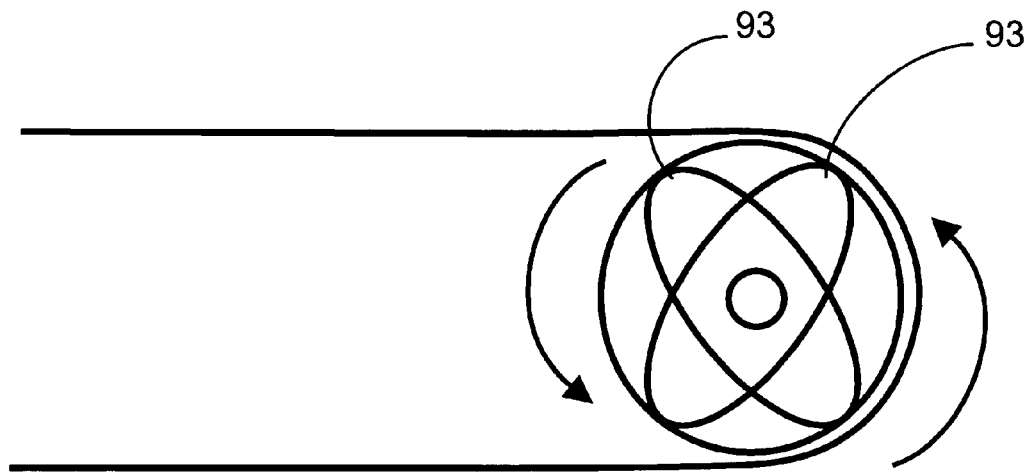

Referring to FIG. 9, a primary coil is shown having a configurable geometry. The crossbars 93 are relatively moveable allowing for varying elliptical/circular cross sections of the coils. Using such a configuration, field geometry is modified by moving the crossbars 93 relative to each other.

Even though tissue is described as being between the primary and secondary coils throughout this disclosure, tissue located within the magnetic field is of concern. Essentially, tissue that is between the coils in the sense of being within the magnetic field and not physically between the coils is intended. Skin and other tissue within the magnetic field is affected by the field and conversely affects the field.

Numerous other embodiments may be envisaged without departing from the spirit and scope of the invention.

What is claimed is:

1. In a TET device having a primary coil and a primary coil driver for operation outside a living organism, and a secondary coil for implanting within the living organism the two coils for being coupled by a magnetic field, a system for tuning the TET device comprising:

a) means for measuring at least a characteristic of the secondary coil during operation and for transmitting an indication of the characteristic from within the organism to outside the organism;

b) means for receiving the transmitted indication of the characteristic and for providing a signal related to said indication; and, c) a control circuit for receiving the signal related to said indication and for controlling a characteristic of the magnetic field in order to effect a change in the saturation point of the magnetic field.

2. The system for tuning the TET of claim 1 wherein the characteristic of the magnetic field is controlled by varying the frequency of the power provided to the primary coil.

3. The system for tuning the TET of claim 1 wherein the characteristic of the magnetic field is field geometry.

4. The system for tuning the TET of claim 1 wherein the characteristic of the magnetic field is controlled by varying the shape of the induced magnetic field.

5. The system for tuning the TET of claim 4 wherein a winding of the primary coil is provided with a plurality of taps and wherein the shape of the magnetic field is varied by switching between the taps to alter a driven portion of the primary coil.

6. The system for tuning the TET of claim 1 wherein the characteristic of the secondary coil is related to coupling efficiency between the first and second coils.

7. The system for tuning the TET of claim 1 wherein the characteristic of the secondary coil is related to load on the second coil.

8. In a TET device having a primary coil and a primary coil driver for operation outside a living organism, and a secondary coil for implanting within the living organism the two coils for being coupled by a magnetic field, a system for tuning the TET device comprising:

a) means for measuring at least a characteristic of the secondary coil relating to power coupling efficiency during operation and for transmitting an indication of the characteristic from within the organism to outside the organism;

b) means for receiving the transmitted indication of the characteristic and for providing a signal related to said indication; and, C) a control circuit for receiving the signal related to said indication and for effecting a change in the saturation point of the magnetic field.

9. In a TET device having a primary coil and a primary coil driver for operation outside a living organism, and a secondary coil for implanting within the living organism, a system for tuning the TET device comprising:

a) means for measuring at least a characteristic of the secondary coil during operation and for transmitting an indication of the characteristic from within the organism to outside the organism;

b) means for receiving the transmitted indication of the characteristic and for providing a signal related to said indication; and, c) a voltage control circuit for receiving the signal related to said indication and for independently controlling voltage and current in the primary coil in dependence upon the received signal.

10. The system for tuning the TET of claim 9 wherein the characteristic includes induced voltage.

11. The system for tuning the TET of claim 9 wherein the characteristic includes load current.

* * * * *